United States Patent [19]
Bronstein et al.

[11] Patent Number: 6,162,610
[45] Date of Patent: Dec. 19, 2000

[54] XANTHAN-ESTER AND ACRIDAN SUBSTRATES FOR HORSERADISH PEROXIDASE

[75] Inventors: Irena Bronstein, Newton; Brooks Edwards, Cambridge; John Voyta, Sudbury; Rouh-Rong Juo, Allston, all of Mass.

[73] Assignee: Tropix, Inc., Bedford, Mass.

[21] Appl. No.: 09/152,247

[22] Filed: Sep. 11, 1998

[51] Int. Cl.$^7$ ............... G01N 33/533; C07D 219/04; C07D 311/82; C07D 335/12; C12N 9/96

[52] U.S. Cl. ............... 435/7.92; 435/6; 435/28; 435/188; 435/968; 546/102; 546/104; 549/24; 549/223; 549/225

[58] Field of Search ............... 435/188, 6, 7.92, 435/28, 968; 546/104, 102; 549/24, 223, 225

[56] References Cited

U.S. PATENT DOCUMENTS

| | | |
|---|---|---|
| 5,241,070 | 8/1993 | Law et al. ............... 546/107 |
| 5,290,936 | 3/1994 | Beheshti et al. ............... 546/104 |
| 5,523,212 | 6/1996 | Akhavan-Tafti et al. . |
| 5,593,845 | 1/1997 | Akhavan-Tafti et al. . |

*Primary Examiner*—Mary E. Ceperley
*Attorney, Agent, or Firm*—Piper Marbury Rudnick & Wolfe LLP; Steven B. Kelber

[57] ABSTRACT

Xanthan esters and acridans are substrates for horseradish peroxidase. These stable, enzymatically cleavable chemiluminescent esters are substrates for horseradish peroxidase which, together with peroxide is among the extensively used enzyme in enzyme-linked detection methods, including immunoassays, oligonucleotide detection and nucleic acid hybridization. The novel compounds are used, together with peroxide, alkali and the peroxidase, to indicate the presence and/or concentration of target compounds. The assays may be enhanced by the use of polymeric quaternary onium enhancement compounds or similar compounds selected to enhance the chemiluminescence emitted.

24 Claims, No Drawings

XANTHAN-ESTER AND ACRIDAN SUBSTRATES FOR HORSERADISH PEROXIDASE

BACKGROUND OF THE INVENTION

1. Field of the Invention

This invention relates to chemiluminescent, enzymatically activatable, xanthan-esters and hydroxy acridan esters which are substrates for horseradish peroxidase. This invention further relates to the incorporation of these xanthan-esters and acridans in immunoassays, chemical assays and nucleic acid probe assays to permit an analyte—the chemical or biological substance whose presence, amount or structure is being determined—to be identified or quantified. Assay methods may be used to detect and quantitate various biological molecules including haptens, antigens and antibodies by the technique of immunoassay, proteins by Western blotting, DNA and RNA by Southern and Northern blotting respectively.

2. Description of Related Art

The detection and quantitation of biological molecules has been accomplished with several types of "labels" including radioisotopic, enzymatic, and phosphorescent/fluorescent. Typically, a detection method employs at least one analytical reagent that binds to a specific target macromolecular species or hapten and produces a detectable signal. These analytical reagents typically have two components: (1) a probe macromolecule, for example, an antibody or oligonucleotide, that can bind a target molecule with a high degree of specificity and affinity, and (2) a detectable label, such as a radioisotope or covalently linked fluorescent dye molecule. In general, the binding properties of the probe macromolecule define the specificity of the detection method, and the detectability of the associated label determines the sensitivity of the detection method. The sensitivity of detection is in turn related to both the type of label employed and the quality and type of equipment available to detect it.

Radioisotopic labels have several disadvantages, such as potential health hazards, difficulty in disposal, special licensing requirements and instability (radioactive decay and radiolysis).

Recently, numerous non-radioactive methods have been developed to avoid the hazards and inconvenience posed by these materials. Examples of such non-radioactive labels include: (1) enzymes that catalyze conversion of a chromogenic substrate to an insoluble, colored product (e.g. alkaline phosphatase, β-galactosidase, horseradish peroxidase) or catalyze a reaction that yields a fluorescent or luminescent product, and (2) direct fluorescent labels (e.g. fluorescein, isothiocyanate, rhodamine, Cascade blue), which absorb electromagnetic energy in a particular absorption wavelength spectrum and subsequently emit visible light at one or more longer (i.e. less energetic) wavelengths.

Fluorescent labels do not offer the signal amplification advantage of enzyme labels, but they do possess significant advantages which have resulted in their widespread adoption in immunocytochemistry. Fluorescent labels typically are small organic dye molecules, such as fluorescein, Texas Red, or other rhodamines, which can readily be conjugated to probe molecules, such as immunoglobulins or *Staph. aureus* Protein A. The fluorescent molecules (fluorophores) can be detected by illumination with light of an appropriate excitation frequency and the resultant spectral emissions can be detected by electro-optical sensors or light microscopy.

Methods based on enzyme-linked analytes offer the best sensitivity since a single enzyme molecule typically has a persistent capacity to catalyze the transformation of a chromogenic substrate into detectable product. With appropriate conditions and incubation time, a single enzyme molecule can produce a large amount of product and hence yield considerable signal amplification. Substrates which generate color, fluorescence or chemiluminescence have been developed, the latter achieving the best sensitivity.

Chemiluminescent compounds which have been used in the prior art include aminophthalhydrazides, acridans, acridinium esters and dioxetanes. U.S. Pat. No. 5,593,845 discloses chemiluminescent N-alkylacridancarboxylate derivatives which allow the production of light from the acridan by reaction with a peroxide and a peroxidase. U.S. Pat. No. 5,686,258, discloses that the above mentioned reaction can be enhanced by the addition of a phenolic enhancer. U.S. Pat. No. 5,670,644, discloses improved acridan compounds which, upon reaction with a peroxidase enzyme and a peroxide compound, are converted into a more persistent, intermediate acridinium compound, wherein the center ring is aromatic, which subsequently undergoes a rapid chemiluminescent reaction when the pH is raised. U.S. Pat. No. 5,679,803 discloses chemiluminescent 1,2-dioxetanes which can be triggered to decompose and chemiluminesce by either enzymatic triggering agents or chemical triggering agents.

Among the enzymes used in enzyme-linked detection methods such as immunoassays, detection of oligonucleotides and nucleic acid hybridization techniques, the most extensively used to date has been horseradish peroxidase. Amino-substituted cyclic phthalhydrazides such as luminol and isoluminol react with $H_2O_2$ and a peroxidase enzyme catalyst (such as horseradish peroxidase) under basic conditions with emission of light. This reaction has been used as the basis for analytical methods for the detection of $H_2O_2$ and for the peroxidase enzyme. Various enhancers have been employed in conjunction with the use of luminol to increase the intensity of light emitted. These include D-luciferin, p-iodophenol, p-phenylphenol and 2-hydroxy-9-fluorenone. A more complete list of peroxidase enhancers useful with compounds of this invention can be found in U.S. Pat. No. 5,206,149 (Oyama, et al.), which is incorporated by reference. Commercially available kits for conjugation of HRP with enhanced luminol chemiluminescent detection are available.

Chemiluminescent substrates known in the art do not permit full advantage to be taken of the beneficial properties of horseradish peroxidase in analysis mainly due to sensitivity limitations. A substrate which permits the detection of lower amounts of enzyme is needed to enable the use of peroxidase conjugates in applications requiring ultrasensitive detection. Specifically, substrates are required which generate higher levels of chemiluminescence without an accompanying increase in the background or non-specific chemiluminescence. The increased chemiluminescence may be accomplished via either a higher maximum intensity or a longer duration than compounds known in the art.

SUMMARY OF THE INVENTION

This invention provides a new class of stable, enzymatically activatable chemiluminescent 9-carboxy xanthan esters, thioesters, and sulfonimides which are substrates for horseradish peroxidase. The invention also encompasses enzymatically activatable chemiluminescent hydroxy acridan esters or thioesters as substrates for horseradish peroxidase (HRP). These substrates are capable of reacting in aqueous media, e.g., in a sample of biological fluid in solution or on a solid surface, e.g. a membrane surface such as a nylon membrane, with HRP or an HRP modified specific binding pair to release optically detectable energy.

These substrates are useful in light emitting chemical compositions containing the instant compounds, horseradish peroxidase, enhancers, hydrogen peroxide and alkali.

The present invention also relates to a method for producing chemiluminescence which comprises reacting a xanthan ester or a hydroxy acridan-9H-carboxylic acid ester or thioester with horseradish peroxidase, hydrogen peroxide and alkali.

The present invention also relates to a chemiluminescent composition comprising a xanthan ester or a hydroxy acridan substrate, horseradish peroxidase, optimally enhancers, hydrogen peroxide and alkali.

The present invention also relates to kits for detecting the presence or amount of an analyte in an assay procedure by a chemiluminescent reaction.

These chemiluminescent substrates also find particular utility in methods for determining whether an analyte is present in a sample. The enzyme may be the target analyte in the sample inspected, or it may be a reporter molecule attached to a probe, antigen, antibody, or any member of a specific binding pair, to detect the presence of the other member of the specific binding pair. The chemiluminescent substrate is activated by horseradish peroxidase, hydrogen peroxide and alkali. The amount of luminescence generated is then detected and related to the amount of analyte in the sample.

DETAILED DESCRIPTION OF THE INVENTION

The novel chemiluminescent xanthan-esters or thioxanthan esters of this invention can be represented by the formula:

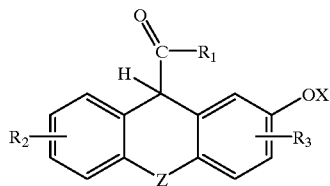

wherein $R_2$ and $R_3$ may be attached to any carbon atom on the xanthene ring and may independently be hydrogen, alkyl, branched alkyl, substituted alkyl, alkoxy, halogen, nitro, amino, acylamino, carboxamide, carboxylic ester, aryl, e.g., phenyl and naphthyl, heteroaryl, e.g., 2-benzothiazol-2-yl, aryloxy or any fluorophore which will exhibit efficient energy transfer from the excited xanthone moiety. The substituents on the alkyl group can be for example, groups which enhance the water solubility of the xanthan ester, such as carboxylic acids, carboxylate salts, esters, ethers, amines, oligomeric and polymeric ammonium salts, heteroalkyl groups, heteroalkoxy groups, sugars, sulfonic acids or their salts, and quaternary amino salt groups. When $R_2$ or $R_3$ are not fluorophores, $R_2$ or $R_3$ may be additionally substituted with any fluorophore which will exhibit efficient energy transfer from the excited xanthone moiety or any groups which allow attachment of any fluorophore which will exhibit efficient energy transfer from the excited xanthone moiety, so long as they do not interfere with the production of light;

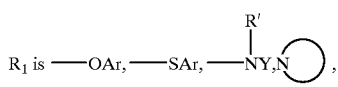

an alkyl or branched alkyl group which is substituted with one or more fluorine atoms, or any leaving group which allows the production of light from the xanthan ester by reaction with a peroxide and a peroxidase;

can be any nitrogen containing heterocyclic ring which can also contain carbon, other heteroatoms or additional fused rings, wherein the N atom is bonded to the carbonyl group of the xanthan ester and wherein the ring may also be substituted with $R_2$ and/or $R_3$ groups as defined above. However, the heterocycle must also have art-recognized utility as a leaving group. Examples include: pyrazole, imidazole, benzimidazole, benzotriazole, and tetrazole;

Ar is a substituted or unsubstituted aryl group such as phenyl or naphthyl. Preferred substituents on Ar include: one or more electron withdrawing groups, e.g., perfluoroalkyl having from 1 to 7 carbon atoms, such as trifluoromethyl; alkyl or arylsulfonyl, such as methylsulfonyl; halogen, such as fluoro or chloro; cyano; nitro; alkoxycarbonyl, such as —COOEt; alkanoyl, such as —COCH$_3$; amidosulfonyl, such as —SO$_2$NHAr, or $C_1$–$C_7$ alkyl or substituted alkyl groups specifically located ortho to the attachment point of $R_1$ in order to sterically stabilize the CO—YR$_1$ linkage;

Y is a substituted or unsubstituted aryl sulfonyl, e.g., phenyl or naphthyl, or alkyl sulfonyl group, such as CF$_3$SO$_2$, ArSO$_2$, wherein the S atom is bonded to the N atom of the

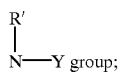

R' is an alkyl, aryl or substituted aryl group, wherein the substituents on the aryl group are the same as those which may be used as substitutents on —Ar as recited above, e.g., one or more electron withdrawing groups, etc;

X is hydrogen or any enzymatically cleavable group; and
Z is O or S.

Examples of the fluorophores which comprise $R_2$ and/or $R_3$ include:

1) phenyl and phenyl derivatives;
2) naphthalene and naphthalene derivatives, e.g. 5-dimethylaminonaphthalene-1-sulfonic acid and hydroxy naphthalene;
3) anthracene and anthracene derivatives, e.g. 9,10-diphenylanthracene, 9-methylanthracene, 9-anthracene carboxaldehydre, anthryl alcohols and 9-phenylanthracene;
4) rhodamine and rhodamine derivatives, e.g. rhodols, tetramethyl rhodamine, tetraethyl rhodamine, diphenyldimethyl rhodamine, diphenyldiethyl rhodamine, dinaphthyl rhodamine;
5) fluorescein and fluorescein derivatives, e.g. 5-iodoacetamido fluorescein, 6-iodoacetamido fluorescein, and fluorescein-5-maleimide;
6) eosin and eosin derivatives, e.g., hydroxyeosins, eosin-5-iodoacetamide; and eosin-5-maleimide;

7) coumarin and coumarin derivatives, e.g., 7-dialkylamino-4-methylcoumarin, 4-bromomethyl-7-methoxycoumarin, and 4-bromomethyl-7-hydroxycoumarin;

8) crythrosin and crythrosin derivatives, e.g., hydroxy erythrosins, erythrosin-5-iodoacetamide and erythrosin-5-maleimide;

9) aciridine and acridine derivatives, e.g., hydroxy aciridines and 9-methyl aciridine;

10) pyrene and pyrene derivatives, e.g., N-(1-pyrene) iodoacctamide, hydroxy pyrenes, and 1-pyrenemethyl iodoacctate;

11) stilbene and stilbene derivatives, e.g., 6,6'-dibromostilbene and hydroxy stilbenes;

12) nitrobenzoxadiazoles and nitrobenzoxadiazole derivatives, e.g., hydroxy nitrobenzoxadiazoles, 4-chloro-7-nitrobenz-2-oxa-1,3-diazol, 2-(7-nitrobenz-2-oxa-1,3-diazolc-4-yl-amino)hexanoic acid;

13) quinoline and quinoline derivatives, e.g., 6-hydroxyquinoline and 6-aminooquinoline;

14) acridine and acridine derivatives, e.g., N-methylacridine and N-phenylacridine;

15) acidoacridine and acidoacridine derivatives, e.g., 9-methylacidoacridine and hydroxy-9-methylacidoacridine;

16) carbazole and carbazole derivatives, e.g., N-methylcarbazole and hydroxy-N-methylcarbazole;

17) fluorescent cyanines, e.g., DCM (a laser dye), hydroxy cyanines, 1,6-diphenyl-1,3,5-hexatriene, 1-(4-dimethyl aminophenyl)-6-phenylhexatriene, and the corresponding 1,3-butadiences.

18) carbocyanine and carbocyanine derivatives, e.g., phenylcarbocyanine and hydroxy carbocyanines;

19) pyridinium salts, e.g., 4(4-dialkyldiaminostyryl) N-methyl pyridinium iodate and hydroxy-substituted pyridinium salts;

20) oxonols; and 21) resorofins and hydroxy resorofins.

Examples of the enzymatically cleavable group X include: phosphate, α- or β galactoside, acetate, 1-phospho-2,3-diacylglyceride, 1-thio-D-glucoside, adenosine triphosphate, adenosine monophosphate, adenosine, α-D-glucoside, β-D-glucoside, β-D-glucurnide, α-D-mannoside, β-D-mannoside, β-D-fructofuranoside, β-D#glucosiduronate, P-toluenesulfonyl-L-arginine ester, P-toluenesulfonyl-L-arginine amide, phosphoryl choline, phosphoryl inositol, phosphoryl ethanolamine, phosphoryl serine, diacylglycerol phosphate diester and monoacylglycerol phosphate diester.

When X is an enzymatically cleavable group, it is necessary to add an enzyme which cleaves X. Examples of such enzymes include: alkaline and acid phosphatases, esterases, decarboxylases, phospholipase D, β-xylosidase, βD-fucosidase, thioglucosidase, β-D-galactosidase, α-D-galactosidase, α-D-glucosidase, β-D-glucosidase, α-D-mannosidase, β-D-mannosidase, β-D-fructofuranosidase, β-D-glucosiduronase, and trypsin. A list of which enzymes cleave which of the various X groups can be found in Table I of U.S. Pat. No. 5,605,795, which is incorporated by reference herein.

Preferred substrates include 2-hydroxy-9H-9-xanthenecarboxylic acid, phenyl ester and 3-hydroxy-9H-9-xanthene-carboxylic acid, phenyl ester. The invention also encompasses acridans of the following formula:

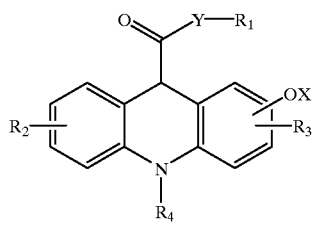

wherein $R_1$ is Ar. Ar is a substituted or unsubstituted aryl group such as phenyl or naphthyl. Preferred substituents on Ar include: one or more electron withdrawing groups, e.g., perfluoroalkyl having from 1 to 7 carbon atoms, such as trifluoromethyl; alkyl or arylsulfonyl, such as methylsulfonyl; halogen, such as fluoro or chloro; cyano; nitro; alkoxycarbonyl, such as —COOEt; alkanoyl, such as —COCH$_3$; amidosulfonyl, such as —SO$_2$NHAr, or $C_1$–$C_7$ alkyl or substituted alkyl groups specifically located ortho to the attachment point of $R_1$ in order to sterically stabilize the CO—YR$_1$ linkage.

$R_4$ is aryl, aralkyl, alkyl or branched alkyl which may be further substituted with halogen, carboxyl, carboxylic acid ester, amino, nitro, hydroxyl or sulfur-containing groups, oligomeric and polymeric ammonium salts, sugars, sulfonic acids or their salts, quaternary ammonium groups or any group which enhances the water solubility of the acridan.

Y is oxygen, sulfur or

can be any nitrogen containing heterocyclic ring which can also contain carbon, other heteroatoms or additional fused rings and wherein the N atom is bonded to the carbonyl group of the acridan. However, the heterocycle must also have art-recognized utility as a leaving group. Examples include: pyrazole, imidazole, benzimidazole, benzotriazole, and tetrazole;

$R_2$ and $R_3$ may be attached to any free carbon atom on the xanthene ring and may independently be hydrogen, alkyl, branched alkyl, substituted alkyl, alkoxy, halogen, nitro, amino, acylamino, carboxamide, carboxylic ester, aryl, e.g., phenyl and naphthyl, heteroaryl, e.g., 2-benzothiazol-2-yl, aryloxy or any fluorophore which will exhibit efficient energy transfer from the excited xanthone moiety. The substituents on the alkyl group can be for example, groups which enhance the water solubility of the xanthan ester, such as carboxylic acids, carboxylate salts, esters, ethers, amines, oligomeric and polymeric ammonium salts, heteroalkyl groups, heteroalkoxy groups, sugars, sulfonic acids or their salts, and quaternary amino salt groups; and X can be hydrogen or any enzymatically cleavable group.

Reaction of the above mentioned xanthan esters and acridans with a peroxide, horseradish peroxidase, enhancers and alkali produces chemiluminescence with superior properties for assay applications. Although Applicant does not wish to be limited to a mechanism, the chemiluminescence is believed to arise from the excited state of the oxyxanthone anion (via xanthan ester) or oxyacridone anion (via hydroxyacridan ester) as shown in the reaction schemes below.

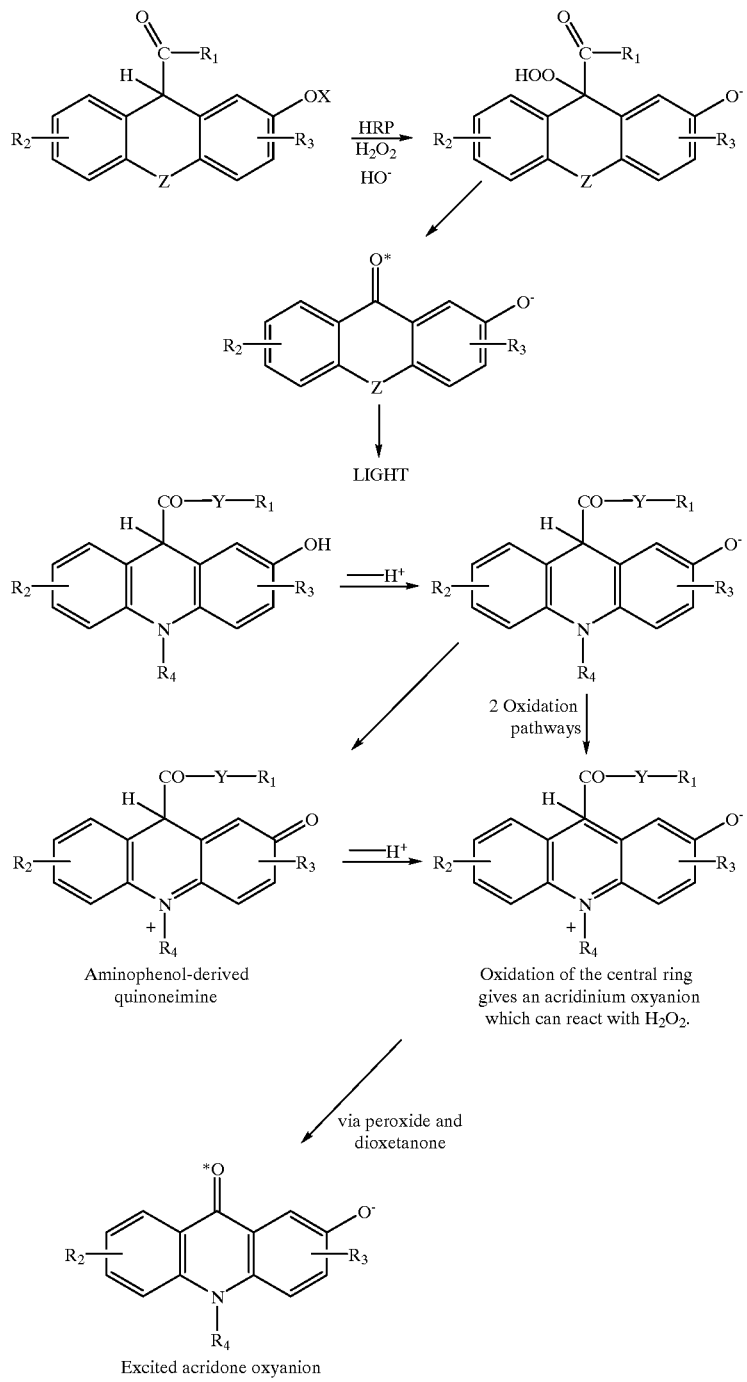

The xanthan ester or the hydroxy acridan ester is added to a sample, suspected of containing the target analyte, which has been mixed with an enzyme complex which will bind to or otherwise co-act with the target analyte, if present in the sample. The xanthan ester or the acridan is therefore a co-substrate along with hydrogen peroxide for the horseradish peroxidase, the enzyme-catalyzed oxidation with resulting cleavage of the leaving group from the body of the xanthan ester or acridan resulting in the excited state of the oxyanion (xanthone) or oxyanion (acridone) which produces light. Where the target analyte in the sample is the HRP itself, the xanthan ester or acridan is added directly to the sample, either as drawn, or after preliminary clarification to reduce turbidity. Where the target analyte is other than the HRP, the HRP is complexed with a binding moiety, such as a DNA probe or antibody, so as to bind to the target analyte present in the sample. The amount of chemiluminescence detected will be responsive to both the analyte in the sample, and the amount of analyte in the sample.

To enhance the chemiluminescent signal, and improve signal/noise (S/N) ratio to permit discrimination between background signals and positive target-responsive signals at very low levels, a water soluble enhancement agent is added to the sample prior to or concomitant with the introduction of the xanthan ester or acridan substrate. Examples of water-soluble enhancement agents include polymeric quaternary amines, neutral detergents and cationic detergents. Particularly effective are the polymeric onium salts, e.g. quaternary salts based on phosphonium, sulfonium and, preferably, ammonium moieties. These polymeric onium salts are disclosed in U.S. Pat. No. 5,547,836, which is incorporated by reference herein, as enhancement agents for 1,2-dioxetanes. Poly(vinylbenzyltributylammonium chloride) (TBQ) is particularly effective in increasing the chemiluminescent signal produced by the excited oxyanions. Table 1 below shows the strong enhancement of signal and signal to noise ratio produced by a quaternary onium polymer.

Enhancers which may be used to enhance the action of the peroxidase enzyme include 4-iodophenol and 4-phenylphenol, among others.

EXAMPLES

Effect of Detergents and Polymers on Chemiluminescent Signal From 3-Hydroxy-9H-9-xanthene-carboxylic acid phenyl ester (14)

Detergent was added to the buffer solution to increase the solubility of the assay components. The use of polymeric quaternary amines, neutral detergents and cationic detergents was compared using polyvinylbenzyltributylammonium chloride (Sapphire II, Tropix), Tween-20 (Sigma) and cetyltrimethylammonium chloride (CTAB, Sigma). Luminescence was measured in white opaque microplate wells using a Dynatech ML3000 luminometer. First, background signal was measured after the addition of hydrogen peroxide (10 μL of 3.5 mM stock solution) to 0.12 mL of 1.17 mM xanthene substrate (14) in 0.1 M citrate buffer pH 7.0 containing, 0.42 mg/mL hydroxypropylmethylcellulose and 4-iodophenol (iodophenol concentration was 71.4 μg/mL for the Sapphire II and Tween-20 solutions and 178.6 μg/mL for the CTAB solution) after a 19 minute incubation. HRP, 10 μL containing 5 fmol, was added to each well and the chemiluminescence was measured after a 19 min incubation. The results of this comparison are shown in Table 1.

TABLE 1

|  | Sapphire II | Tween-20 | CTAB |
| --- | --- | --- | --- |
| Background | 14.83 | 0.0242 | 2.45 |
| Signal + HRP | 229.05 | 0.0439 | 3.78 |
| S/N | 15.4 | 1.8 | 1.5 |

Comparison of Xanthene Substrate (14) and Enhanced Chemiluminescence (ECL)

The following conditions were used for the comparison of ECL(a commercially available optimized reagent containing Luminol-an amino-substituted cyclic acylhydrazide) and Xanthene substrate (14). ECL reagents were obtained from Amersham and were used as recommended by the manufacturer. Aliquots of horseradish peroxidase (HRP, Type VIA), 10 μL, containing 0,0.5, 5.0, 50.0, 500.0 and 5000.0 attomoles HRP were then added to 0.13 mL of each reagent formulation. To evaluate Xanthene substrate, hydrogen peroxide (10 μL of a 3.5 mM stock) was added to 10 μL of each HRP dilution and the reaction was initiated by addition of a solution of 0.12 mL of 1.17 mM Xanthene substrate in 0.1 M citrate buffer pH 7.0 containing 1.22 mM 4-phenylphenol, 0.42 mg/mL hydroxypropylmethylcellulose and 0.167 mg/mL Emerald II. The chemiluminescent signal was measured in a Dynatech ML3000 luminometer after 1 minute for ECL and 40 minutes for Xanthene substrate. The results of this comparison are shown in Table 2.

TABLE 2

|  | Xanthene (14) | | ECL | |
| --- | --- | --- | --- | --- |
| HRP, amol | RLU | S/N | RLU | S/N |
| 0.5 | 14.12 | 1.11 | 0.075 | 1.25 |
| 5 | 17.52 | 1.37 | 0.11 | 1.83 |
| 50 | 63.12 | 4.95 | 0.15 | 2.50 |
| 500 | 353.31 | 27.70 | 4.02 | 67.00 |
| 5000 | 740.51 | 58.06 | 89.47 | 1491.17 |

As can be seen from the data, the xanthan ester provides a much greater light intensity as measured in RLUs, with an acceptable signal to noise (S/N) ratio, as compared to the enhanced chemiluminescence of the prior art. High signal readout is particularly important for microarray formats where small volumes of reagents must be used.

The xanthan esters can be synthesized as shown below.

Synthetic Protocols

SCHEME 1
2-hydroxy-9H-9-xanthene-carboxylic acid, phenyl ester 7.

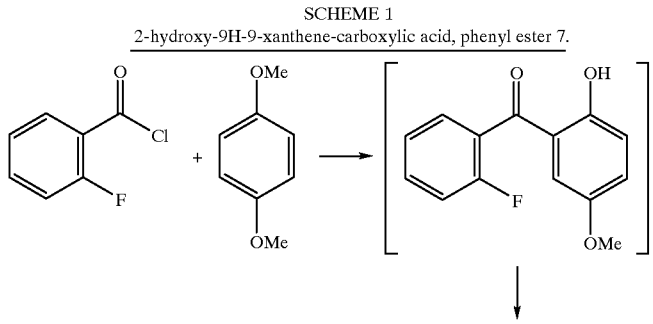

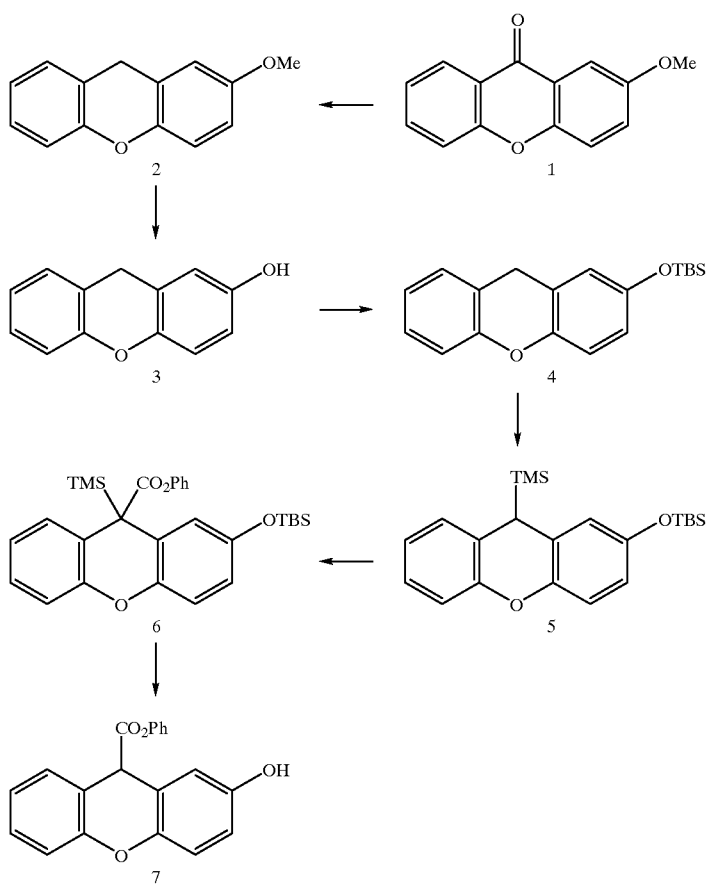
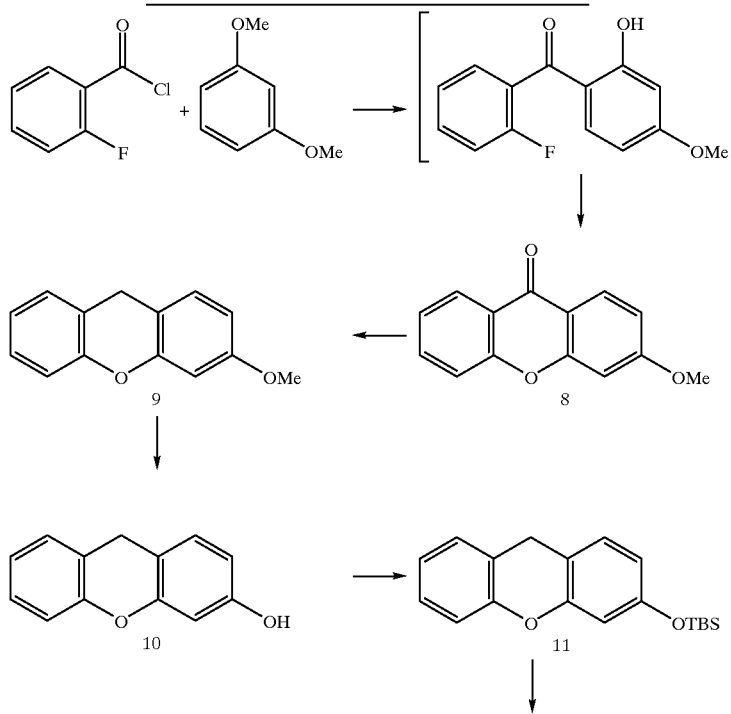
SCHEME 2
3-hydroxy-9H-9-xanthene-carboxylic acid, phenyl ester 14.

-continued

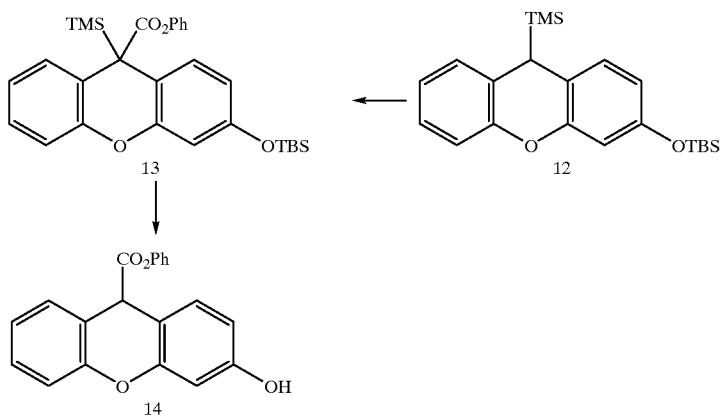

The acridans can be synthesized as shown below.

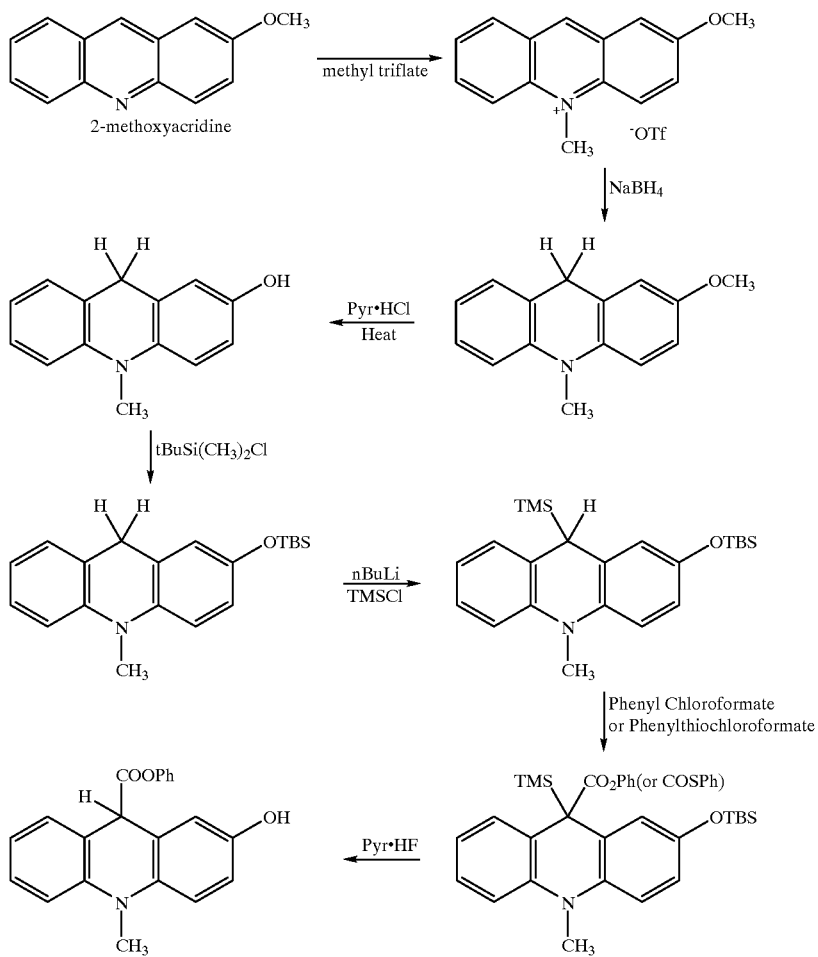

Experimental Section

2-Methoxy-9H-xanthen-9-one (1). A mixture of 2-fluorobenzoyl chloride (15.86 g, 0.1 mole) and 1,4-dimethoxybenzene (13.82 g, 0.1 mole) in 1,2-dichloroethane (200 ml) was cooled in an ice bath and treated cautiously with $AlCl_3$ (13.82 g, 0.103 mole) portionwise. The temperature of the reaction mixture was kept at 0–5° during the addition, and then warmed to room temperature over 4 hrs after completion of addition. The resulting deep red reaction mixture was further refluxed for 1.5 hrs, followed by stirring at room temperature overnight. The reaction was quenched by addition of ice and 6N HCl solution in an ice bath with continued stirring at 0° for an hour. The mixture was then extracted three times with $CH_2Cl_2$. The combined organic layers were washed with 50% NaCl solution, dried over anhydrous $Na_2SO_4$ and filtered through a silica gel plug, yielding the intermediate benzophenone (24.68 g, 100%) as an orange colored oil which was used for cyclization without further purification. IR (neat): 3070, 2998, 2936, 2736, 1605, 1477, 1445, 1328, 1265, 1226, 1212, 1135, 1038, 960, 870, 792, 758 and 646 $cm^{-1}$.

The benzophenone intermediate was then stirred in EtOH (400 ml) at room temperature and treated with a solution of NaOMe in MeOH (25 wt. %, 45.72 ml, 0.2 mole). The color of the reaction mixture changed to burgundy right away. The reaction mixture was brought to reflux for 1 hr and 20 min, TLC showed that the reaction was complete. After brief cooling, water (500 ml) was added while the mixture was still warm and a yellow powder precipitated. The suspension was stored in refrigerator overnight. The solid was filtered on a Buchner funnel and washed with cold water. 2-Methoxy-9H-xanthen-9-one 1 (20.7 g, 91.6%) was obtained as a light yellow powder: m.p. 128–130° C.; $^1$H NMR ($CDCl_3$): delta 8.33 (1H, dd, J=7.9, 1.8 Hz), 7.67–7.72 (2H, m), 7.47 (1H, d, J=8.6 Hz), 7.42 (1H, d, J=9.2 Hz), 7.35 (1H, m), 7.31 (1H, dd, J=9.2, 3.1 Hz) and 3.90 (3H, s); 1R ($CHCl_3$): 2998, 1635, 1610, 1480, 1463, 1430, 1313, 1266, 1140, 1108, 1038, 852 and 823 $cm^{-1}$.

2-Methoxy-9H-xanthene (2). To a suspension of lithium aluminum hydride (1.75 g, 46 mmole) in $Et_2O$ (100 ml) at 0° was added dropwise a slightly cloudy solution of xanthone 1 (3.34 g, 14.8 mmole) in toluene (84 ml) over 10 min. After removal of the ice bath, the mixture was stirred at room temperature for an hour, then refluxed at 120–125° for 18 hrs. TLC of the small aliquot showed that no starting material remained. The reaction was cooled in ice, while the excess lithium aluminum hydride was destroyed carefully by dropwise addition of EtOAc (1 ml), MeOH (1 ml) and finally, dilute HCl solution until the aqueous layer was acidic. The reaction mixture was partitioned between 5% EtOAc-hexanes and water. After the organic layer was separated, the aqueous layer was extracted two more times with 5% EtOAc-hexanes. The combined organic layers were washed with 50% NaCl solution, dried over anhydrous $Na_2SO_4$ and filtered through a silica gel plug. The silica gel was flushed with 100 ml of 5% EtOAc-hexanes. After concentration of the filtrate, the crude 2-methoxy-9H-xanthene 2 (3.09 g, 98.7%) was collected as a light yellow powder: mp 66–68° C.

Xanthene 2 was stored in a vial under argon, wrapped with tin foil and kept in refrigerator without further purification. $^1$H NMR ($CDCl_3$): delta 7.13–7.19 (2H, m), 6.95–7.02 (3H, m), 6.74 (1H, dd, j=7.9, 3.1 Hz), 6.68 (1H, d, J=2.4 Hz), 4.02 (2H, s), and 3.77 (3H, s); 1R ($CHCl_3$): 2998, 2930, 2830, 1578, 1478, 1455, 1240, 1147, 1035 and 878 $cm^{-1}$.

2-Hydroxy-9H-xanthene (3). A solid mixture of 2-methoxy-9H-xanthene 2 (3.09 g, 14.6 mmole) and pyridine hydrochloride (23.85 g, 206.4 mmole) was heated at 200–210° for 1.5 hrs. The resulting reaction mixture was cooled to about 80° and treated with water, while a white powder dropped out of solution. The suspended mixture was stirred at ambient temperature and then cooled to 0°. The solid was filtered on a Buchner funnel and washed with cold water. A large quantity of $CH_2Cl_2$ was needed to redissolve the crude product. The $CH_2Cl_2$ solution was washed with dilute HCl solution. The aqueous layer was extracted with $CH_2Cl_2$. The combined organic layers were dried over anhydrous $Na_2SO_4$. TLC showed a small by-product at the origin, but neither of the starting material nor the oxidation product, 2-hydroxy-9H-xanthene-9-one, was formed. The $CH_2Cl_2$ solution was filtered through a silica gel plug, the silica gel was flushed with 20% EtOAc-hexanes (100 ml). After concentration of the filtrate, the crude 2-hydroxy-9H-xanthene 3 (2.68 g, 93%) was collected as a slightly yellow powder: mp 137–139° C. $^1$H NMR (DMSO-$d_6$): delta 9.18 (1H, s), 7.14–7.22 (2H, m), 6.97–7.03 (2H, m), 6.87 (1H, dd, J=7.3, 1.8 Hz), 6.57–6.62 (2H, m) and 3.94 (2H, s).

2-tert-Butyldimethylsiloxy-9H-xanthene (4). A solution of 2-hydroxy-9H-xanthene 3 (2.63 g, 13.28 mmole) in DMF (15 ml) was added imidazole (1.36 g, 19.9 mmole), t-butyldimethylsilyl chloride (2.4 g, 15.92 mmole) and DMAP (15 mg) successively at room temperature. The mixture was allowed to stir overnight (16 hrs) and quenched with saturated $NaHCO_3$ solution. The aqueous layer was extracted two times with 10% EtOAc-hexanes. The combined organic layers were washed with water, dried over anhydrous $Na_2SO_4$ and concentrated. The light orange oily residue was loaded onto a silica gel plug and eluted with hexanes and then 3% EtOAc-hexanes. The relatively clean fractions of the desired product were pooled and concentrated, yielding the slightly impure 2-tert-butyldimethylsiloxyl-9H-xanthene 4 (3.297 g, 79.5%) as an off-white solid: mp 67–69° C. $^1$H NMR ($CDCl_3$): delta 7.12–7.19 (2H, m), 6.96–7.01 (2H, m), 6.89 (1H, d, J=8.5 Hz), 6.61–6.67 (2H, m), 3.98 (2H, s), 0.97 (9H, s) and 0.17 (6H, s); 1R ($CHCl_3$): 2960, 2938, 1630, 1587, 1487, 1464, 1251, 1203, 1158, 1120, 976, 892, 868 and 843 $cm^{-1}$.

The impure fractions were concentrated separately and chromatographed on a short silica gel column, affording an additional TBS protected xanthene 4 (0.571 g, 13.8%).

2-tert-Butyldimethylsiloxy-9H-9-trimethylsilyl-xanthene (5). A solution of 2-tert-butyldimethylsiloxy-9H-xanthene 4 (3.297 g, 10.57 mmole) in THF (47 ml) was treated with 2.37 M n-BuLi in hexane (8.9 ml, 21.1 mmole) dropwise at −78° over 5 min. The resulting deep red mixture was stirred from −78° to 0° over 2 hrs continuing at 0° for an hour. Cooled back to −78°, trimethylsilyl chloride (3.35 ml, 26.4 mmole) was added dropwise. The mixture was stirred from −78° to 0° for 70 min, followed by dilution with hexanes and quenching with saturated $NaHCO_3$ solution. After the organic layer was separated, the aqueous layer was extracted with hexanes. The combined organic layers were washed with water, dried over anhydrous $Na_2SO_4$ and filtered through a silica gel plug. The filtrate was concentrated, yielding the crude 2-tert-butyldimethylsiloxy-9H-9-trimethylsilyl-xanthene 5 (4.19 g, 100%) as an orange colored waxy solid.

$^1$H NMR ($CDCl_3$): delta 7.07 (1H, m), 6.92–6.97 (3H, m), 6.84 (1H, d, J=8.8 Hz), 6.55 (1H, m), 6.43 (1H, d, J=2.9 Hz), 3.29 (1H, s), 0.97 (9H, s), 0.16 (6H, s) and −0.05 (9H, s); 1R ($CHCl_3$): 2960, 2938, 2962, 1625, 1608, 1480, 1240, 1350, 1098, 976, 890 and 843 $cm^{-1}$.

2-tert-butyldimethylsiloxy-9-trimethylsilyl-9-xanthene carboxylic acid, phenyl ester (6). A solution of the slightly impure 2-tert-butyldimethylsiloxy-9H-9-trimethylsilyl-xanthene 5 (4.19 g, 10.57 mmole) in THF (50 ml) was added dropwise the 2.37 M n-BuLi in hexanes (9.8 ml, 23.3 mmole) at −78°. The resulting deep red solution was stirred from −78° to −15° for 3.5 hrs, then cooled back to −78°. Phenyl chloroformate (3.3 ml, 26.4 mmole) was added dropwise, and the resulting mixture was stirred from −78° to 10° for 1.5 hrs, and then at room temperature for an additional hour. Finally, the orange colored reaction mixture was diluted with hexanes and quenched with saturated $NaHCO_3$ solution. After the organic layer was separated, the aqueous layer was extracted two times with 5% EtOAc-hexanes. The combined organic layers were washed with water, dried over anhydrous Na$_2$SO$_4$ and filtered through a silica gel plug. The crude product exhibited three ester absorptions with different intensities as observed in the 1R spectrum. Purification was performed by silica gel chromatography, eluting with 2% EtOAc-Hex, to furnish 5.7804 g of the still impure product as a green colored solid. Fortunately, the pure phenyl ester of 2-tert-butyldimethylsiloxy-9-trimethylsilyl-9-xanthene carboxylic acid 6 (1.38 g, 25.9% overall yield from 4) was obtained as an off-white solid: m.p. 111–113° by recrystallization in MeOH. Pure 6 showed a single spot on TLC and exhibited a single absorption at 1734 cm$^{-1}$ in the 1R. $^1$H NMR (CDCl$_3$): delta 7.33–7.38 (2H, m), 7.0–7.23 (7H, m), 6.92 (1H, d, J=8.4 Hz), 6.69 (1H, dd, J=8.8, 2.9 Hz), 6.61 (1H, d, J=2.6 Hz), 0.97 (9H, s), 0.17 (6H, s) and 0.04 (9H, s).

IR (CHCl$_3$): 2960, 2938, 2862, 1734, 1483, 1415, 1268, 1238, 1185, 1120, 995, 901, 878 and 843 cm$^{-1}$.

2-Hydroxy-9H-9-xanthene-carboxylic acid, phenyl ester (7). A suspended mixture of 2-tert-butyldimethylsiloxy-9-trimethylsilyl-9-xanthene-carboxylic acid phenyl ester, 6 (570 mg, 1.13 mmole), in CH$_3$CN (10 ml) and pyridine (2 ml) became a clear yellow solution after a brief stirring at room temperature. The mixture was treated with 20 drops of 48% HF from a pipette and stirred for 3 hrs at room temperature. The reaction mixture was quenched with dilute HCL solution, followed by two extractions with 30% EtOAc-hexanes. The combined organic layers were washed with water, dried over anhydrous Na$_2$SO$_4$ and concentrated. The residue was dissolved in a minimum amount of 2% MeOH-CH$_2$Cl$_2$ and chromatographed on a silica gel column, eluting with CH$_2$Cl$_2$ to 2% MeOH-CH$_2$Cl$_2$. The relatively clean fractions were pooled and concentrated. The impure yellow product was further purified by trituration first with 5% EtOAc-hexanes followed by hexanes, yielding pure phenyl 2-hydroxy-9H-9-xanthene-carboxylate 7 ((173.5 mg, 48.3%) as a slightly yellow solid: mp 182–184° C.; $^1$H NMR (DMSO-d$_6$): delta 7.33–7.40 (3H, m), 7.24 (1H, m), 7.13–7.17 (2H, m), 7.04 (1H, d, J=8.8 Hz), 6.95–6.98 (2H, m), 6.90 (1H, d, J=2.6 Hz), 6.78 (1H, dd, J=8.8, 2.6 Hz) and 5.40 (1H, s).

3-Methoxy-9H-xanthen-9-one (8). To a mixture of 2-fluorobenzoyl chloride (6 ml, 50 mmole) and 1,3-dimethoxybenzene (6.9 g, 50 mmole) in 1,2-dichloroethane (120 ml) was added AlCl$_3$ (6.84 g, 51.3 mmole) portionwise at 0 to 5°. The resulting dark brown mixture was allowed to warm to room temperature over 3.5 hrs, and then refluxed for an hour. Cooling to 0°, the reaction was quenched carefully with 6N HCl solution, while a large amount of aluminum salts dropped out of solution. The mixture was further diluted with CH$_2$Cl$_2$ and water and stirred at room temperature until a clear two-phased mixture resulted. After the organic layer was separated, the aqueous layer was extracted two times with CH$_2$Cl$_2$. The combined organic layers were washed with water, dried over anhydrous Na$_2$SO$_4$ and filtered through a silica gel plug. Concentration of the filtrate, gave the substituted benzophenone intermediate (12.51 g, 100%) as an orange colored gum, which was used for cyclization without further purification. 1R (neat): 3070, 3068, 3000, 2964, 2937, 2836, 1598, 1482, 1447, 1346, 1275, 1255, 1205, 1163, 1115, 1098, 1024, 968, 920 and 758 cm$^{-1}$.

A solution of the benzophenone intermediate (12.51 g) in EtOH (200 ml) was treated with a solution of NaOMe in MeOH (25 wt. %, 22.86 ml, 0.1 mole) at room temperature, the color of the mixture changed from yellow to orange immediately. The reaction mixture was brought to reflux for 100 min. Cooled to 0°, the reaction mixture was treated with water (100 ml), to produce a fine white precipitate. The solid was filtered on a Buchner funnel, washed with water and EtOH, and finally dried in vacuo, yielding 3-methoxy-9H-xanthen-9-one 8 (9.12 g, 80.7%) as a white powder: m.p. 127–129° C.; $^1$H NMR (CDCl$_3$): delta 8.31 (1H, dd, J=7.9, 1.2 Hz), 8.23 (1H, J=8.6 Hz), 7.68 (1H, m), 7.44 (1H, d, J=8.6 Hz), 7.35 (1H, m), 6.93 (1H, m), 6.87 (1H, d, J=2.4 Hz) and 3.92 (3H, s); 1R (CHCl$_3$): 2999, 1644, 1605, 1460, 1434, 1321, 1273, 1254, 1159, 1101, 1029, 968 and 848 cm$^{-1}$.

3-Methoxy-9H-xanthene (9). To a suspension of lithium aluminum hydride (0.524 g, 13.8 mmole) in Et$_2$O (30 ml) at 0° was added, dropwise, a solution of xanthone 8 (1 g, 4.42 mmole) in toluene (25 ml). The resulting mixture was stirred at room temperature for 30 min, then refluxed vigorously for 17 hrs. After cooling in an ice bath, the reaction was quenched carefully with EtOAc (1.5 ml), MeOH (1.5 ml) and finally with dilute HCl solution until the aqueous layer was acidic. The reaction mixture was partitioned between 10% EtOAc-hexanes and water. After the organic layer was separated, the aqueous layer was extracted two more times with 10% EtOAc-hexanes. The combined organic layers were washed with saturated NaCl solution, dried over anhydrous Na$_2$SO$_4$ and filtered through a silica gel plus. After concentration of the filtrate, 3-methoxy-9H-xanthene 9 (0.806 g, 86%) was isolated as a slightly yellow solid: m.p. 72–74° C.; $^1$H NMR (CDCl$_3$): delta 7.13–7.20 (2H, m), 6.98–7.06 (3H, m), 6.58–6.62 (2H, m), 3.97 (2H, s) and 3.79 (3H, s); 1R (CHCl$_3$): 3000, 2935, 2836, 1625, 1596, 1520, 1480, 1455, 1438, 1275, 1227, 1150, 1119, 1092, 1031, 962 and 837 cm$^{-1}$.

3-Hydroxy-9H-xanthene (10). A solid mixture of 3-methoxy-9H-xanthene 9 (5.84 g, 27.5 mmole) and pyridine hydrochloride (42 g, 363 mmole) was heated at 200–210° for 2 hrs. The resulting reaction mixture was cooled to about 70° and treated with water, while a precipitate formed. The orange colored solid was filtered on a Buchner funnel, washed with water, and dried in vacuo, yielding the crude 3-hydroxy-9H-xanthene 10 (5.25 g, 96%). No major oxidation took place when crude 10 was stored in a desiccator under argon in the dark. Thus, the crude xanthene 10 was used for silylation without further purification. No $^1$H NMR or 1R were taken.

3-tert-Butyldimethylsiloxy-9H-xanthene (11). To a solution of 3-hydroxy-9H-xanthene 10 (5.25 g, 26.5 mmole) in DMF (21 ml) was added imidazole (1.98 g, 29.15 mmole), t-butyldimethylsilyl chloride (3.99 g, 26.5 mmol) and DMAP (15 mg) successively at room temperature. The resulting light orange reaction mixture was stirred in the dark overnight; no color change occurred. The reaction mixture was poured into a separatory funnel containing saturated NaHCO$_3$ solution and the mixture was extracted two times with 5% EtOAc-hexanes. The combined organic layers were washed with saturated NaCl solution, dried over anhydrous Na$_2$SO$_4$ and filtered through a silica gel plug. After concentration of the filtrate, 6.69 g of the light yellow oil was obtained. The 1R of the crude product 11 exhibited a weak OH absorption at 3340 cm$^{-1}$ from the starting material 10. The crude product was purified by addition of hexanes; a small amount of powder did not go into solution was removed by filtration on a silica gel plug, 3-hydroxy-9H-xanthene 10 (5.4 g, 65.3%) was recovered and showed no OH absorption in 1R . m.p.: 30–32° C.; $^1$H NMR (CDCl$_3$): delta 7.12–7.18 (2H, m), 6.96–7.03 (3H, m), 6.51–6.55 (2H, m), 3.96 (2H, s), 0.97 (9H, s) and #0.2 (6H, s); 1R (neat): 3060, 2942, 2922, 2850, 1623, 1596, 1568, 1478, 1300, 1266, 1231, 1150, 1110, 1091, 980, 883 and 750 cm$^{-1}$.

3-tert-Butyldimethylsiloxy-9H-9-trimethylsilyl-xanthene (12). A solution of 3-tert-butyldimethylsiloxy-9H-xanthene 11 (2.44 g, 7.8 mmole) in THF (34 ml) was treated with 2.37 M BuLi in hexane (6.9 ml, 16.38 mmole) dropwise at −78°. The resulting red mixture was stirred from −78° to 5° for 2 hrs and continued at 0° for an hour. Cooled back to −78°, trimethylsilyl chloride (2.5 ml, 19.5 mmole) was added dropwise. The mixture was slowly warmed to 0° over 2 hrs, diluted with hexanes, and quenched with saturated $NaHCO_3$ solution. After the organic layer was separated, the aqueous layer was extracted with hexanes. The combined organic layers were washed with water, dried over anhydrous $Na_2SO_4$ and filtered through a silica gel plug, yielding 3-t-butyldimethylsiloxy-9H-9-xanthene 12 (3.12 g, 100%) as an orange gum. TLC of 12 showed faint spots above and below the product. However, no purification the product was necessary for subsequent reaction. $^1H$ NMR ($CDCl_3$): delta 6.47–7.07 (7H, m), 3.29 (1H, s), 0.97 (9H, s), 0.18 (6H, s) and −0.08 (9H, s); 1R (neat): 3066, 3040, 2958, 1628, 1605, 1483, 1268, 1236, 1157, 1100, 988, 842 and 755 $cm^{-1}$.

3-tert-butyldimethylsiloxy-9-trimethylsilyl-9-xanthene carboxylic acid, phenyl ester (13). A solution of the crude 3-tert-butyldimethylsiloxy-9H-9-trimethyl-silyl-xanthene 12 (3.12 g, 7.8 mole) in THF (40 ml) was added dropwise to the 2.37 M BuLi in hexanes (7.2 ml, 17.16 mmole) at −78°. The resulting deep red solution was stirred at −78 to 15° over 3.5 hrs, and then cooled back to −78°. Phenyl chloroformate (2.4 ml, 19.5 mmole) was added dropwise. The mixture was stirred from −78 to 10° for 2 hrs and at room temperature for 30 min. After dilution with hexanes, the mixture was poured into a separatory funnel containing saturated $NaHCO_3$ solution. After the organic layer was separated, the aqueous layer was extracted twice with 2% EtOAc-hexanes. The combined organic layers were washed with water, dried over anhydrous $Na_2SO_4$ and filtered through a silica gel plug, yielding 5.91 g of an orange gum. The crude product showed three ester absorptions at 1730–1780 $cm^{-1}$ in the 1R spectrum. Chromatography of the crude product, furnished phenyl 3-tert-butyldimethylsiloxy-9-trimethylsilyl-9-xanthene-carboxylate 13 (3.99 g, 100%) as a still slightly impure yellow gum. The 1R (neat) spectrum displayed absorptions at 3070, 3050, 2960, 2864, 1785, 1765, 1740, 1600, 1487, 1238, 1188, 1120, 1104, 993, 843 and 690 $cm^{-1}$.

3-Hydroxy-9H-9-xanthene-carboxylic acid, phenyl ester (14). A mixture of the crude phenyl (3-tert-butyldimethylsiloxy-9-trimethyl-9-xanthene-carboxylate 13 (1.81 g, 3.59 mmole) in $CH_3CN$ (20 ml) and pyridine (2 ml) was treated with 48% HF from a pipette. The mixture was stirred overnight at room temperature, and then quenched with dilute HCl solution. The aqueous layer was extracted three times with 50% EtOAc-hexanes. The combined organic layers were washed with water, dried over anhydrous $Na_2SO_4$ and filtered through a silica gel plug. The silica gel was flushed with 50% EtOAc-hexanes, and then 2% $MeOH-CH_2Cl_2$, to give 1.38 g of an orange solid. The crude product was triturated three times with 5% EtOAc-hexanes to afford the reasonably clean phenyl ester of 3-hydroxy-9H-9-xanthene carboxylic acid 14 (673.5 mg, 59% overall from 12) as a light orange powder; m.p. 176–178° C.; $^1H$ NMR (DMSO-$d_6$): delta 9.84 (1H, br s), 7.49 (1H, d, J=7.3 Hz), 7.33–7.39 (2H, m), 7.31 (1H, d, J=8.5 Hz), 7.22 (1H, t, J=7.3 Hz), 7.14–7.19 (2H, m), 6.92–6.96 (2H, m), 6.63 (1H, dd, J=8.5, 2.4 Hz), 6.57 (1H, d, J=2.4 Hz) and 5.33 (1H, s).

In the above reactions, substituted-phenyl chloroformates may also readily be utilized. The corresponding thioesters of the substituted-xanthene carboxylic acids are synthesized by using phenylthiochloroformates instead of their oxygen congeners. The above methods are also suitable for the synthesis of hydroxy thioxanthene carboxylic acid phenyl esters or thiophenyl esters which are included in the scope of the invention. The invention also encompasses the use of the parent substitued 9-H-xanthene and 9-H-thioxanthene carboxylic acids to synthesize any acid derivative which contains a suitable leaving group such that subsequent oxidation at the 9-position can produce light from the resultant excited xanthone or thioxanthone oxyanions.

A wide variety of assays exist which use visually detectable means to determine the presence or concentration of a particular substance in a sample (the analyte). The above described xanthan ester and acridan substrates can be used in any of these assays. Examples of such assays include inmunoassays to detect antigens or antibodies, e.g., δ- or β-hCG, hLH, estradiol, etc., chemical assays to detect, e.g., potassium or sodium ions; nucleic acid assays to detect, e.g., viruses (e.g., HTLV III or cytomegalovirus, or bacteria (e.g., E. coli) and certain cell functions (e.g., receptor binding sites). The method of the invention may be used to detect various analytes including: hydrogen peroxide, hydrogen peroxide generated by an enzyme, horseradish peroxidase alone, organic molecules labeled with the peroxidase and biological molecules labeled with the peroxidase.

When the analyte is an antibody, antigen or nucleic acid, the HRP is preferably bonded to a substance having a specific affinity for the analyte (i.e., a substance that binds specifically to the analyte), e.g. an antigen, an antibody or a nucleic acid probe. Conventional methods, e.g., carbodiimide coupling, are used to bond the HRP to the specific affinity substance; bonding is preferably through an amide linkage.

In general, assays are performed as follows. A sample suspected of containing the analyte of interest is contacted with a buffered solution containing an HRP bonded to a substance having a specific affinity for the detectable substance. The resulting solution is incubated to allow the detectable substance to bind to the specific affinity portion of the specific affinity-HRP complex. Excess specific affinity-HRP complex is then washed away, and a xanthan ester or acridan having a leaving group cleavable by the HRP portion of the specific affinity-enzyme compound is added. The HRP cleaves the leaving group causing the xanthan ester or acridan to become excited and luminesce. Luminescence is detected (using, e.g., a cuvette, or light sensitive film in a camera luminometer, or a photoelectric cell or photomultiplier tube), as an indication of the presence of the analyte in the sample. Luminescence intensity is measured to determine the concentration of the analyte.

The present invention also relates to a kit for detecting the presence or amount of an analyte in an assay procedure by a chemiluminescent reaction, which comprises in one or more containers:

(a) a xanthan ester or acridan substrate;

(b) horseradish peroxidase (optionally attached to an analyte binding compound)

(c) hydrogen peroxide;

(d) alkali;

(e) optionally a second enzyme for cleaving the X moiety; and (f) optionally a membrane, e.g., nylon or nitrocellulose and wherein the chemiluminescence is detected in the assay procedure by reacting the xanthan ester or acridan substrate with the peroxide and the peroxidase#(optionally attached to the analyte binding compound) and optionally the second enzyme which cleaves the X moiety, in the presence of alkali to thereby detect the analyte in the sample. The reaction may be carried out in solution such as an aqueous buffer or on the surface of a solid support such as a bead, tube, microwell plate or a membrane as is well known to those skilled in the art.

Examples of specific assays follow:

A. Assay for Human Leutinizing Hormone

The concentration of hLH in human serum is measured as described here. To a 12 mm×75 mm glass test tube, 50 μL of a patient's serum, urine or standard and 20 μL of a horseradish peroxidase conjugated monoclonal anti-α-hLH is added and mixed. Then, a 0.25 inch monoclonal anti-β-hLH coated polystyrene bead is added, mixed, incubated for 1 hour on a rotator, reaction mixture is removed, washed twice with 2 mL of 0.1% Tween-20 in phosphate buffered saline and residual wash solution is carefully aspirated. 30 μL of hydrogen peroxide is added and 360 μL of Xanthene substrate formulation prepared as described in the previous section, incubated for 30 minutes and the chemiluminescence intensity is measured in a suitable luminometer. The concentration of hLH in the patient's sample is determined by comparing the sample's chemiluminescence intensity to the standard curve data.

B. Estradiol Immunoassay

A competitive immunoassay for estradiol is formatted as described here. 100 μL of patient's sample or standards and 100 μL of diluted estradiol-HRP conjugate are added to rabbit anti-estradiol coated polystyrene 12 mm×75 mm tubes and incubated for 1 hour at room temperature on a rotator. Reaction mixture is removed, tubes washed twice with 2 mL of 0.1% Tween-20 in phosphate buffered saline, residual wash solution carefully aspirated, 30 μL of hydrogen peroxide and 360 μL of Xanthene substrate formulation prepared as described in the previous section are added, incubated for 30 minutes and the chemiluminescence intensity measured in a suitable luminometer. The concentration of hLH in the patient sample is determined by comparing the sample's chemiluminescence intensity to the standard curve data.

Furthermore, these xanthan ester based substrates for peroxidases can be utilized in many cell based assays such as to measure interaction of endothelin in inflammatory diseases, in the direct determination of plasma NO of septic patients, detection of transcription factor mediated sepsis, investigation of phagocytosis and the respiratory bursts, and measurement of antioxidant capacities in biological fluids and tissues.

What is claimed is:

1. A chemiluminescent substrate for the detection of horseradish peroxidase comprising a xanthan ester of the following formula:

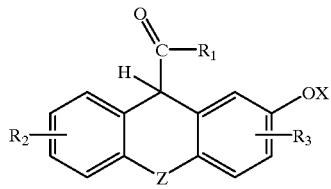

wherein

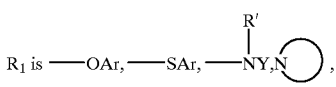

an alkyl or branched alkyl group of 1–20 carbon atoms which is substituted with one or more fluorine atoms or any leaving group which allows the production of light from the xanthan ester by reaction with a peroxide and a peroxidase; $R_2$ and $R_3$ may be attached to any free carbon atom on the xanthene ring and may independently be hydrogen, alkyl, branched alkyl, substituted alkyl, alkoxy, each containing 1–20 carbon atoms, halogen, nitro, amino, acylamino, carboxamide, carboxylic ester, aryl, heteroaryl, aryloxy or any fluorophore which will exhibit efficient energy transfer from an excited xanthone moiety;

may be any nitrogen containing heterocyclic ring which functions as a leaving group and which can also contain carbon, other heteroatoms or additional fused rings, wherein the N atom is bonded to the carbonyl group of the xanthan ester and wherein the ring may also be substituted with $R_2$ and/or $R_3$ groups as defined above;

Ar is a substituted or unsubstituted aryl group;

R' is an alkyl, aryl or substituted aryl group;

Y is a substituted or unsubstituted aryl sulfonyl or alkyl sulfonyl group, wherein the S atom is bonded to the N atom of the

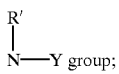

X is hydrogen or any enzymatically cleavable group; and
Z is O or S.

2. The chemiluminescent substrate of claim 1 wherein the xanthan ester is selected from the group consisting of 2-hydroxy-9H-9-xanthene-carboxylic acid, phenyl ester and 3-hydroxy-9H-9-xanthene-carboxylic acid, phenyl ester.

3. A chemiluminescent substrate for the detection of horseradish peroxidase comprising an acridan of the formula:

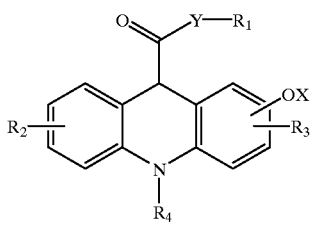

wherein $R_1$ is a substituted or unsubstituted aryl group wherein said substituted aryl group bears one or more groups selected from the group consisting of perfluoroalkyl having from 1 to 7 carbon atoms; alkyl or arylsulfonyl; halogen; cyano; nitro; alkoxycarbonyl; alkanoyl; amidosulfonyl; and $C_1$–$C_7$ alkyl or substituted alkyl groups located ortho to the attachment point of $R_1$;

$R_4$ is aryl, aralkyl, alkyl or branched alkyl which may be further substituted with halogen, carboxyl, carboxylic acid ester, amino, nitro, hydroxyl, heteroalkyl, heteroalkoxy, or sulfur-containing groups, oligomeric and polymeric ammonium salts, quaternary amino salt groups, sugars, sulfonic acids or their salts or any group which enhances the water solubility of the compound;

Y is oxygen, sulfur or

wherein

may be any nitrogen containing heterocyclic ring which functions as a leaving group and which can also contain carbon, other heteroatoms or additional fused rings, wherein the N atom is bonded to the carbonyl group of the xanthan ester and wherein the ring may also be substituted with $R_2$ and/or $R_3$ groups as defined below;

$R_2$ and $R_3$ may be attached to any free carbon atom on the xanthene ring and may independently be hydrogen, alkyl, branched alkyl, substituted alkyl, alkoxy, each containing 1–20 carbon atoms, halogen, nitro, amino, acylamino, carboxamide, carboxylic ester, aryl, heteroaryl, aryloxy or any fluorophore which will exhibit efficient energy transfer from an excited xanthone moiety; and X is hydrogen or any enzymatically cleavable group.

4. A method for producing chemiluminescence which comprises reacting a xanthan ester substrate of claim 1 or an acridan substrate of claim 3, with horseradish peroxidase, hydrogen peroxide, alkali and optionally a second enzyme which is capable of cleaving the enzymatically cleavable group X from said substrate.

5. The method of claim 4, further comprising adding a polymeric onium salt.

6. The method of claim 5, wherein said polymeric onium salt is poly(vinylbenzyltributylammonium chloride).

7. A chemiluminescent composition comprising a xanthan ester substrate of claim 1 or an acridan substrate of claim 3, horseradish peroxidase, hydrogen peroxide, alkali and optionally a second enzyme which is capable of cleaving the enzymatically cleavable group X from said substrate.

8. The composition of claim 7, further comprising a polymeric onium salt.

9. The composition of claim 8, wherein said polymeric onium salt is poly(vinylbenzyltributylammonium chloride).

10. A kit for conducting an assay for the presence or concentration of analyte in a sample, using a chemiluminescent reaction, which comprises in one or more containers:
    (a) a xanthan ester substrate of claim 1 or an acridan substrate of claim 3;
    (b) horseradish peroxidase;
    (c) hydrogen peroxide;
    (d) alkali;
    (e) optionally a compound which binds specifically to said analyte;
    (f) optionally a second enzyme which is capable of cleaving the enzymatically cleavable X group from said substrate;
    (g) optionally a membrane on which said reaction is performed;
    (h) optionally a compound which binds specifically to said compound which binds specifically to said analyte; and
    (i) optionally a polymeric onium salt.

11. The kit of claim 10 wherein said horseradish peroxidase is attached to said compound which binds specifically to said analyte.

12. The kit of claim 10, wherein said horseradish peroxidase is attached to said compound which binds specifically to said compound which binds specifically to said analyte.

13. The kit of claim 11, wherein said analyte is a nucleic acid or fragment thereof and said compound which binds specifically to said analyte is an oligonucleotide probe, complementary to said nucleic acid or fragment thereof, which is covalently attached to said horseradish peroxidase.

14. The kit of claim 12, wherein said analyte is a nucleic acid or fragment thereof, said compound which binds specifically to said analyte is a complementary oligonucleotide probe which is covalently labeled with an antigen and said compound which binds specifically to said compound which binds specifically to said analyte is an antibody directed to said antigen, which is covalently bound to said horseradish peroxidase and wherein said kit includes said membrane.

15. The kit of claim 11 wherein said compound which binds specifically to said analyte is a monoclonal antibody which is conjugated to said horseradish peroxidase.

16. The kit of claim 10 wherein said kit includes an analyte selected from the group consisting of hydrogen peroxide, horseradish peroxidase, organic molecules labeled with horseradish peroxidase and biological molecules labeled with horseradish peroxidase.

17. The kit of claim 10, wherein said compound which binds specifically to said analyte is a monoclonal antibody and said compound which binds specifically to said compound which binds specifically to said analyte, is conjugated to said horseradish peroxidase.

18. A method of detecting the presence of human leutinizing hormone (hLH) in a sample, comprising:
    (a) adding a horseradish peroxidase conjugated monoclonal anti-α-hLH to said sample and mixing;
    (b) adding anti-β-hLH coated polystyrene beads to the mixture in (a), mixing, incubating, and washing;
    (c) adding hydrogen peroxide and a substrate selected from the group consisting of a xanthan ester of claim 1 and an acridan of claim 3 and optionally a second enzyme which is capable of cleaving the enzymatically cleavable group X from said substrate, to the mixture formed in (b), and incubating;
    (d) measuring chemiluminescence; and
    (e) comparing chemiluminescence to standard curve data to determine the concentration of hLH in said sample.

19. A method of conducting an assay for the presence or concentration of analyte in an aqueous sample, comprising:
    (a) admixing with said sample an enzyme complex comprised of horseradish peroxidase which is coupled to a compound which binds specifically to said analyte;
    (b) removing unbound enzyme complex present in said sample after said admixture;
    (c) adding hydrogen peroxide and a substrate selected from the group consisting of a xanthan ester of claim 1 and an acridan of claim 3 and optionally a second enzyme which is capable of cleaving said enzymatically cleavable group X from said substrate, to said sample, wherein said substrate is caused by the enzyme of said enzyme complex to form an excited state which chemiluminesces; and
    (d) measuring the amount of chemiluminescence obtained, wherein said chemiluminescence is indicative of the presence or concentration of said analyte.

20. The method of claim 19 wherein said compound which specifically binds to said analyte is selected from the group consisting of antibodies, oligonucleotides, haptens and proteins.

21. The method of claim 19 wherein said analyte is selected from the group consisting of estradiol and human leutinizing hormone (hLH).

22. A method of conducting an assay for the presence or concentration of analyte in an aqueous sample, comprising:
   (a) admixing a monoclonal antibody with said sample, which monoclonal antibody will stably bind to said analyte in said sample upon said admixture;
   (b) removing unbound monoclonal antibody present in said sample after said admixture;
   (c) adding an anti-antibody, which is specific for said monoclonal antibody, to which is conjugated horseradish peroxidase, to said sample to form an enzyme complex;
   (d) adding hydrogen peroxide and a substrate selected from the group consisting of a xanthan ester of claim 1 and an acridan of claim 3 and optionally a second enzyme which is capable of cleaving said enzymatically cleavable group X from said substrate, to said sample, wherein said substrate is caused by the horseradish peroxidase of said complex to form an excited state which chemiluminesces; and
   (e) measuring the amount of chemiluminescence obtained, wherein said chemiluminescence is indicative of the presence or concentration of said analyte.

23. The method of claim 22 wherein said analyte is human leutinizing hormone.

24. A method for detecting the presence or concentration of horseradish peroxidase in a sample comprising adding to said sample hydrogen peroxide and a substrate for said horseradish peroxidase, said substrate selected from the group consisting of a xanthan ester of claim 1 and an acridan of claim 3, and measuring the amount of chemiluminescence obtained, wherein said chemiluminescence is indicative of the presence or concentration of horseradish peroxidase.

* * * * *